(12) United States Patent
Banks

(10) Patent No.: US 7,441,953 B2
(45) Date of Patent: Oct. 28, 2008

(54) RADIOGRAPHIC MEDICAL IMAGING SYSTEM USING ROBOT MOUNTED SOURCE AND SENSOR FOR DYNAMIC IMAGE CAPTURE AND TOMOGRAPHY

(75) Inventor: Scott Arthur Banks, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 11/576,868

(22) PCT Filed: Oct. 7, 2005

(86) PCT No.: PCT/US2005/036390

§ 371 (c)(1),
(2), (4) Date: Apr. 6, 2007

(87) PCT Pub. No.: WO2006/042211

PCT Pub. Date: Apr. 20, 2006

(65) Prior Publication Data

US 2008/0037701 A1 Feb. 14, 2008

Related U.S. Application Data

(60) Provisional application No. 60/616,945, filed on Oct. 7, 2004.

(51) Int. Cl.
*H05G 1/02* (2006.01)
(52) U.S. Cl. .......................... 378/197; 378/4
(58) Field of Classification Search ............... 378/8, 378/193, 196–198, 205–206, 4
See application file for complete search history.

(56) References Cited

U.S. PATENT DOCUMENTS 4,894,855 A * 1/1990 Kresse ....................... 378/196
6,064,717 A 5/2000 Ortega et al.
6,435,715 B1 * 8/2002 Betz et al. ................... 378/197

FOREIGN PATENT DOCUMENTS

WO WO 2004/010385 A 1/2004

OTHER PUBLICATIONS

Fantoozai et al. "Fluoroscopic and gait analysis of the functional performance in stair ascent of two total knee replacement designs", Gait and Posture, (2003), vol. 17, No. 3, pp. 225-234.

* cited by examiner

*Primary Examiner*—Hoon Song
(74) *Attorney, Agent, or Firm*—Akerman Senterfitt

(57) ABSTRACT

A radiographic imaging system includes (100) a penetrating radiation source (110) including a first translating device (115), the first translating device (115) comprising a first controller (116) for positioning the radiation source. A radiation detector (120) includes second translating device (125) comprising a second controller for positioning the detector (120). A motion capture device (140) is communicably connected to both the first and second controllers. The motion capture device (140) tracks a position of the subject being imaged and provides position information to both the first controller (116) and second controllers (126) for dynamically coordinating trajectories for both the radiation source (110) and the radiation detector(120). The first and second translating devices preferably comprise robotic arms.

10 Claims, 2 Drawing Sheets

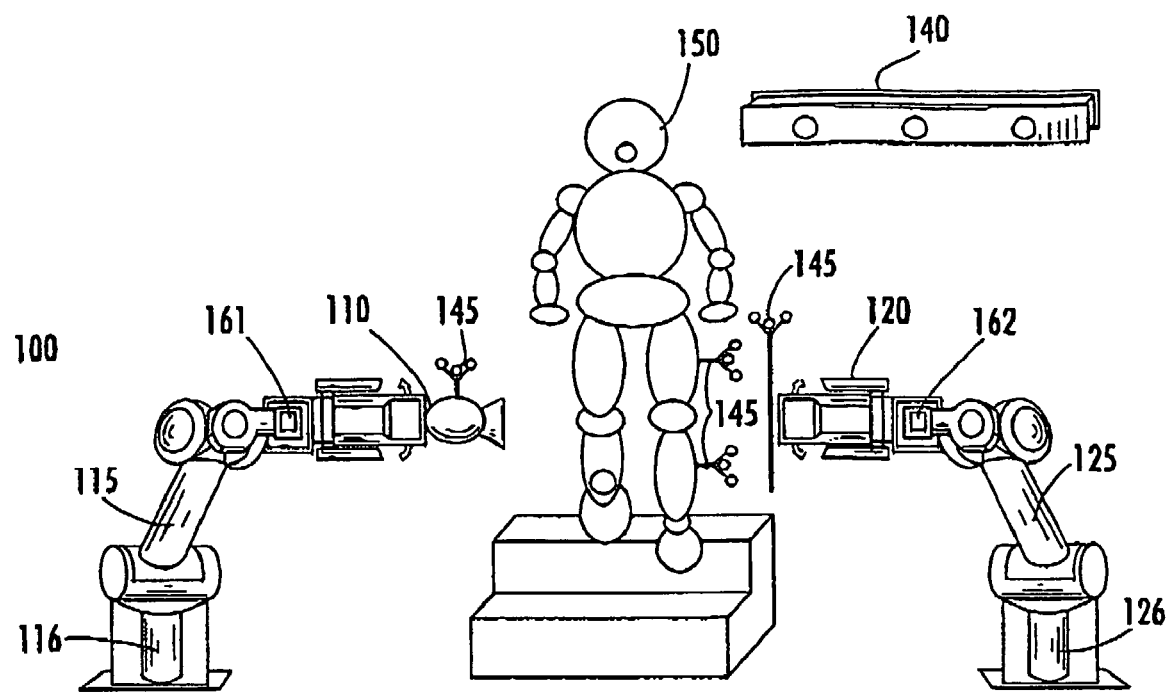
FIG. 1
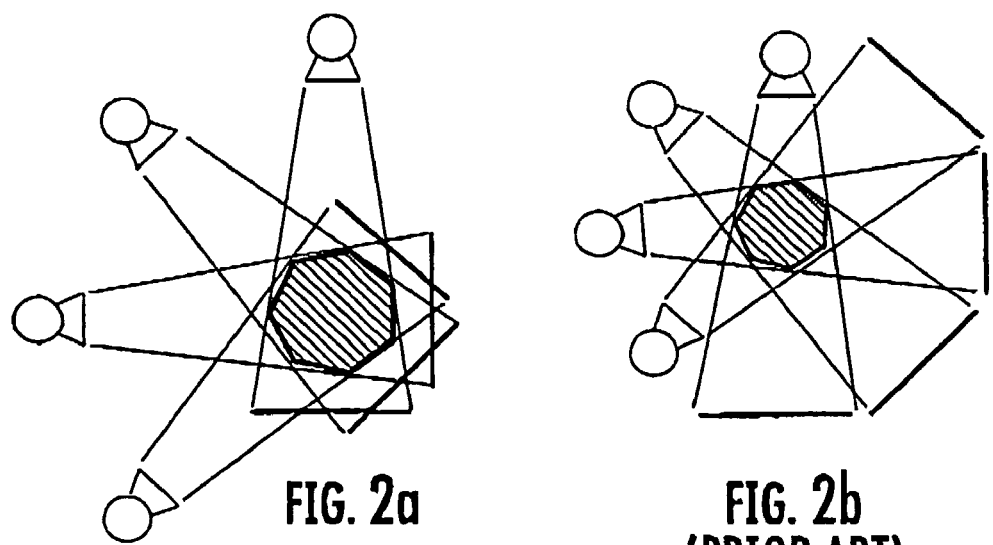
FIG. 2a
FIG. 2b
(PRIOR ART)

RADIOGRAPHIC MEDICAL IMAGING SYSTEM USING ROBOT MOUNTED SOURCE AND SENSOR FOR DYNAMIC IMAGE CAPTURE AND TOMOGRAPHY

CROSS-REFERENCE TO RELATED APPLICATIONS

This application is the national stage entry of International Application No. PCT/US2005/036390, filed Oct. 7, 2005, which claims priority to U.S. Provisional Application No. 60/616,945, filed Oct. 7, 2004.

FIELD OF THE INVENTION

The invention relates to radiographic medical imaging systems using a robotic Mounted source and sensor for dynamic image capture and tomography.

BACKGROUND OF THE INVENTION

Most major musculoskeletal impairments affect the mobile segments of the body, including the synovial (e.g. knees, hips and shoulder) and cartilaginous (e.g. spine, neck) joints. The mobility of these joints can increase or decrease with damage or disease: Osteoarthritis often results in loss of joint motion while ligament or capsular injury of the knee, hip or shoulder results in greater joint motion (laxity). In either case, characterizing joint motion is an important part of the diagnosis and an even more important part of the outcome assessment after treatment.

Unfortunately, accurate assessment of joint motion is challenging. The joints lay beneath layers of skin, muscle and fat that make direct observation or quantification of joint motion difficult. Further complication arises because motion of many joints is significantly influenced by muscle contraction and joint load. Thus, joint motion may differ dramatically depending upon the activity being performed or the muscles activated. These challenges are highlighted in the American Academy of Orthopaedic Surgeons' 2003 Unified Research Agenda which states the following unfilled needs:

1. Study of joint kinematics around the hip, ankle, elbow, shoulder, wrist, and knee in normal, arthritic, and reconstructed states with the development of high-speed computational methodologies to stimulate natural and artificial joint performance.
2. Exploration of the role of novel imaging technologies on joint arthroplasty, including RSA, DEXA, surgical navigation, minimally invasive and robotic surgery.
3. Improving the ability to diagnose spinal disorders, including the ability to localize the source of pain, evaluate motion segment instability, and evaluate the role of muscles and connective tissue on back pain.
4. Study of pathomechanics of joint injury focusing on prevention and the development of more effective protective devices for particular sports and jobs where risks of physical impairment exist.

Each of these items described above requires the ability to measure joint motion or kinematics. This problem has been addressed with a variety of measurement techniques. Methods utilized clinically include serial imaging (radiographs, CT, or MR) with joints stressed in different positions and instrumented laxity testing devices. These techniques permit detailed measurements of joint motion, but do not permit assessment with normal dynamic joint loads or muscle loading.

Motion capture (MoCap) technology also has been used in clinical and research contexts and does permit motion measurement during normal dynamic motion. However, MoCap relies on markers placed at the skin surface, which cannot provide accurate bone motion measures when there is significant muscle/skin/fat overlying the joint, such as the knee, hip, shoulder, or spine.

One solution providing detailed measurement of bone or implant motion during dynamic activity is fluoroscopy, which is essentially x-ray video. In 1991, the present inventor reported the first use of fluoroscopic imaging to quantify two-dimensional (2D) knee replacement motions (Banks S A, Riley P O, Spector C, Hodge W A: In Vivo Bearing Motion with Meniscal Bearing TKR. Orthop Trans 15(2): 544, 1991) and completed a fully three-dimensional (3D) measurement technique based on shape registration in 1992. The present inventor reported further elaborations of this measurement approach and its application to a variety of different devices during a range of activities. This work received international awards, demonstrating the potential for significant worldwide clinical impact. However, the utility of this measurement approach is limited by factors including activity restrictions, anatomy limitations, exposure to ionizing radiation and bone model generation.

Regarding activity restrictions, patients suffering from rupture of the anterior cruciate ligament of the knee can have quite different clinical outcomes depending upon how they recruit their muscles as dynamic joint stabilizers. Similarly, the motions of knee replacements differ significantly depending upon the activity. These findings underscore the need to observe motions during normal loading conditions when deciding on surgical interventions or assessing device design/performance relationships. The challenge is finding clinically important activities where the joint remains in a small volume of space suitable for fluoroscopic observation generally within a 23-30 cm field of view. This challenge has been addressed for the knee by using modified stair-climbing and gait activities where a combination of activity modification and multiple positions of the fluoroscope are used to obtain the required images. However, it has not been possible to observe knee motions during normal ground-level steady walking, stair descent, or chair sit/stand. Furthermore, available imaging systems do not permit observations centered less than ~100 cm from the ground, requiring platforms to elevate the subject into the field of view. This means more equipment is required, the subject is elevated into a visually uncomfortable position, and accessory sensors like floor-mounted force plates for measuring ground reaction forces are not easily used.

Regarding anatomy limitations, "lift with your legs" is a simple, sensible admonition to avoid low back injury. However, it precludes fluoroscopic observation of the low back during relevant lifting activities due to a small field of view. Similarly, it is impossible to obtain a transverse view of the patella, a so-called skyline view, during a chair-rise or bicycle activity without an imaging system that can dynamically align the view to the anatomy of interest. Similar arguments apply to the shoulder, foot & ankle and hip where biomechanically interesting or clinically important observations are not possible because of the limited field of view or immobility of existing radiographic imaging systems.

Regarding exposure to ionizing radiation, fluoroscopy involves exposure to ionizing radiation. Although this often is justified by the clinical need or importance of the information so obtained, exposure must be minimized to the extent possible. Current systems rely on human operators to initiate and terminate exposures. Because the operator has only qualitative feedback on the timing and alignment of the exposure, the patient receives greater than the minimum exposure required for the well aligned & timed diagnostic image sequence.

Regarding bone model generation, the model-based image measurement approach assumes a digital model of the implant or bone surface is available for registration with the radiographic image sequence. Obtaining models for manufactured objects is not difficult. However, it is inconvenient, expensive and time-consuming to obtain separate tomographic scans of the patient or study subject to create the bone-models required for dynamic radiographic motion analysis.

SUMMARY OF THE INVENTION

A radiographic imaging system includes a penetrating radiation source including a first translating device, the first translating device comprising a first controller for positioning the radiation source. A radiation detector includes second translating device comprising a second controller for positioning the detector. A motion capture device is communicably connected to both the first and second controllers. The motion capture device tracks a position of the object being imaged and provides position information to both the first and second controllers for dynamically coordinating trajectories for both the radiation source and the radiation detector. The separate controller aspect of the invention provides a new platform for computed tomography capable of free-form image paths providing greater scan volumes rather than hardware-defined spirals provided by conventional cone-beam computed tomography systems. The first and second translating devices preferably comprise robotic arms. Thus, in this preferred embodiment the system provides cooperative trajectory control of the robotic arms using real-time global feedback information including dynamic object position information regarding the subject being imaged.

The robotic arms include preferably including at least one position sensor. The system can provide unrestricted motion of the source relative to said detector and thus provide cone-beam computed tomography using imaging paths including paths others than a center of rotation located midway between said the source and said detector.

The motion capture device can obtain real time position data for said object, and the system utilizing the real time-data to dynamically guide the first and second controllers. In one embodiment of the invention, the system further comprises at least one of a first force/torque sensor disposed between and end point of the first translating device and the radiation source and a second force/torque sensor disposed between and endpoint of the second translating device and the radiation detector. The system can also include an overhead suspension system to carry a vertical load of a least one of the penetrating radiation source including the first translating device and the radiation detector including the second translating device.

A method of obtaining images comprising the steps of providing a radiographic imaging system which includes a movable and independently positionable penetrating radiation source and radiation image detector, and obtaining dynamic radiographic images of the skeleton of a subject while the subject is in motion using the system, wherein movement of the source and detector is based on motion of the subject to obtain a plurality of aligned views to obtain an image of the subject. The method can further comprise the step of obtaining tomographic scans of the subject, the tomographic scans providing 3D anatomic reconstruction of the subject. In one embodiment of the method, the image detector is placed in contact and remains in contact with the subject while obtaining the dynamic radiographic images. In this embodiment, the images are recorded during weight-bearing activity by the subject.

BRIEF DESCRIPTION OF THE DRAWINGS

There is shown in the drawings embodiments which are presently preferred, it being understood, however, that the invention can be embodied in other forms without departing from the spirit or essential attributes thereof.

FIG. 1 shows an exemplary imaging system according to an embodiment of the invention.

FIG. 2(a) shows the scan volumes provided by a system according to the invention which allows unrestricted "free form" source and sensor motion, while FIG. 2(b) shows the scan volume provided by a conventional cone-beam computed tomography system which uses a center of rotation located midway between the source and sensor.

DETAILED DESCRIPTION OF THE INVENTION

Figure 3:
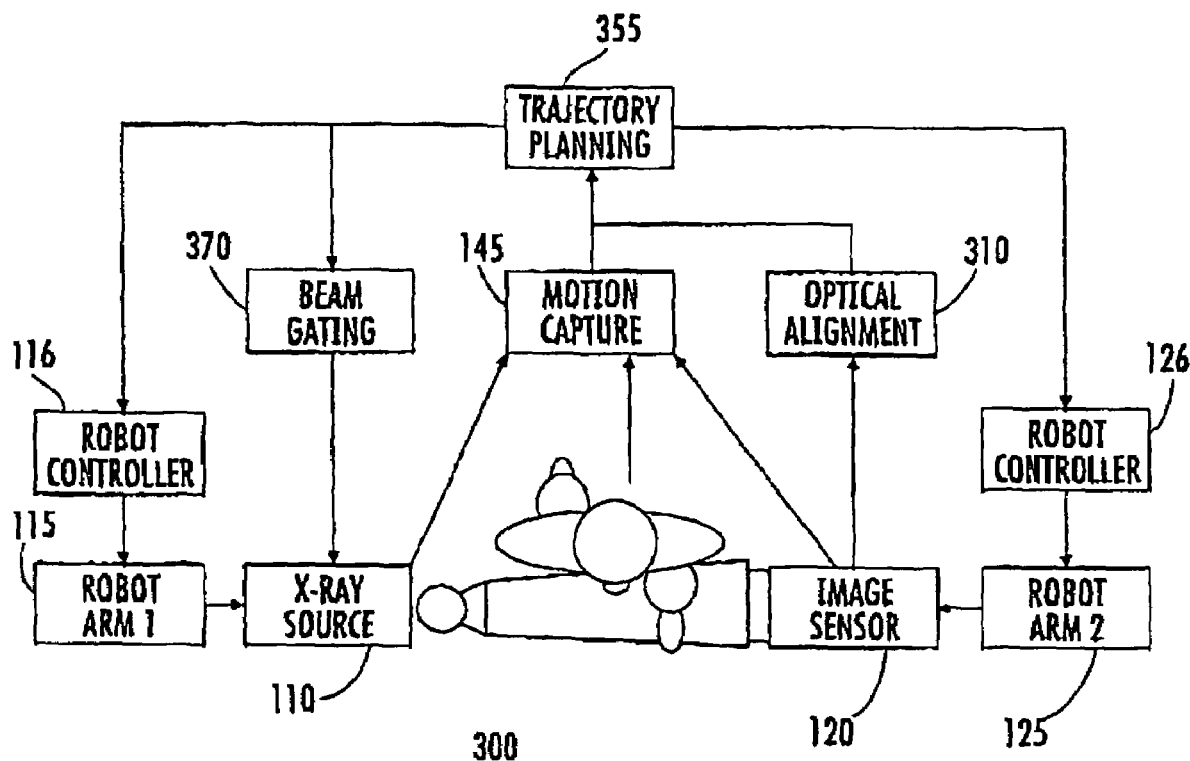
FIG. 3 shows a schematic of an exemplary dynamic imaging system according to the invention which diagrams the communication architecture, according to the invention.

An imaging system 100 according to the invention is shown in FIG. 1 configured for dynamic as well as static imaging of the foot/ankle of patient 150. Although shown in FIG. 1 for foot/ankle measurements, system 100 can be used for dynamic radiographic imaging during natural activities such as walking, stair-climbing and lifting, and easy observation of other parts of the body of patient 150, such as the knee, hip, lumbar spine, cervical spine and shoulder.

The imaging system 100 includes a penetrating radiation source 110 (e.g. x-ray) including a first translating device 115 comprising a position controller 116 for controlling the position of radiation source 110. A gating controller (not shown in FIG. 1) is provided for controlling the timing of emissions from source 110. Radiation detector 120 includes a second translating device 125 comprising a position controller for moving the detector 120. The radiation source 110 and detector 120 are aligned so that radiation from the source 110 passing through the knee of patient 150 is detected by the detector 120. The first and second translating devices are preferably robotic-based as shown in FIG. 1. Regarding the robotics, the system preferably includes coordinated real-time trajectory control of two 6 or 7 axis robotic manipulators.

System 100 also preferably includes a force/torque sensor 161 disposed between the endpoint of translating device 115 and the radiation source 110 and/or a force/torque sensor 162 disposed between the endpoint of translating device 125 and the image detector 120. The force/torque sensors 161 and 162 can be 6-component force/torque sensors. Such force/torque sensors permit additional systems capabilities as described below.

Force/torque sensor 162, supported by appropriate control algorithms, permits the sensor to be moved in contact with the subject 150 to obtain image sequences. One example utilizing this capability, would be to have the image sensor placed against the subject's shin, permitting a so called "sky-line view" view of the patellofemoral joint to be recorded during weight-bearing activity.

Figure 4:
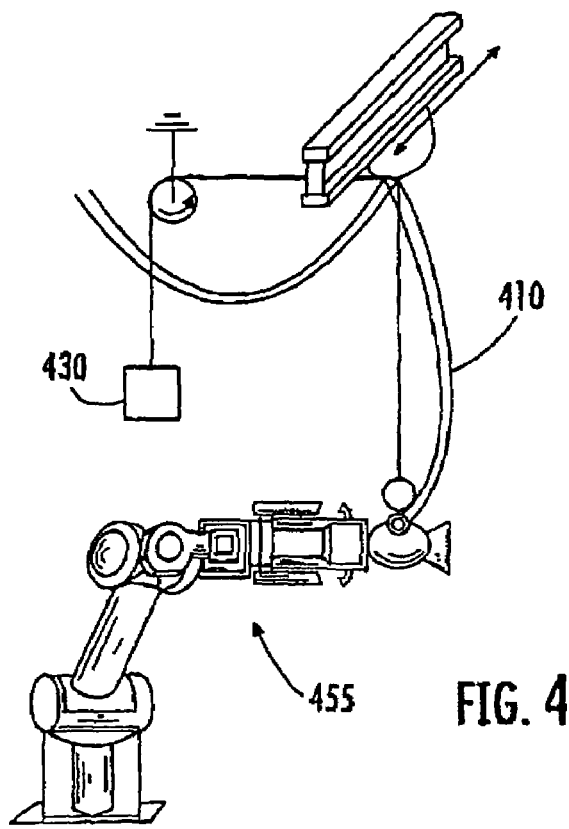
FIG. 4 shows an exemplary mounting sheme for an x-ray source that exceeeds the payload capacity of the robotic translating device.

The system may include a force/torque sensor 161 in support of the radiation source 110 to permit control of a dynamic overhead suspension system (see FIG. 4). This capability would permit a smaller robotic arm to be used to move the radiation source 110, or conversely a larger radiation source 110 to be used with the same size robot.

The penetrating radiation source 110 can comprise an x-ray source, gamma ray source, terahertz source, neutron source or electron beam source. Radiation source 110 preferably illuminates the entire target region of patient 150 to be monitored. The size of the beam can be collimated (collimator not shown in FIG. 1) to any size from about several to tens of square millimeters up to about 40×40 cm$^2$ by the time the beam reaches the patient 150.

System 100 also includes a motion capture device 140. Although not shown in FIG. 1, the motion capture device 140 is secured, such as to a wall or other stationary structure. The motion capture device 140 is communicably connected to both the radiation source controller and the radiation detector controller, such as by wire connection, or more preferably by optical or RF links.

Motion capture device 140 includes or is coupled to a high speed computing device (not shown in FIG. 1) which provides a trajectory planning module. The motion capture device 140 uses real-time motion capture to track the position of patient 150 and provide supervisory control of the robotic imaging system. This type of control structure is known in medical applications, where real-time target position information is used to guide robots performing breast biopsies. This real-time control structure can be used to define the desired trajectory for each robot independently, but imaging performance will generally benefit from a cooperative formulation of the desired trajectory.

The trajectory planning module calculates trajectories in real-time for the radiation source 110 and the radiation detector 120 and appropriate beam gating based on the dynamic position of the knee of patient 150 to achieve the programmed radiographic image capture sequence. As used herein, the term "real time" refers to a fraction of a second processing time typical for electronic circuitry to detect position.

The system will thus use real-time motion capture to measure the movement of patient 150 and pass this information to the robotic system for automatic tracking and gated acquisition of the desired radiographic sequence. This arrangement enables the recordation of joint movements of patient 150 as well as static tomographic scans. In a preferred embodiment, robotically controlled image acquisition paths and cone-beam reconstruction provides the bone surface models required for 2D/3D registration and motion measurement. Thus, system 100 provides both dynamic skeletal imaging and creation of the bone models required for analysis.

As noted above, the translating devices 115 and 125 are preferably robotic arms as shown in FIG. 1. Other translating devices that can be used with the invention include a combination of linear and rotating motorized stages.

Optical markers 145 are shown disposed on patient 150, as well as source 110 and detector 120. Although optical markers 145 are only shown on the end of the robotic translating devices 115 and 125, in a preferred embodiment additional markers will be added on the base of robotic translating devices 115 and 125 to permit easy calibration and allow use of mobile robots.

Markers 145 permit the motion capture device 140 to monitor their respective positions. The motion capture device 140 can track where the various moving parts in system 100 are at any given time in real-time, including direct measurement of the position and orientation of the source 110 and detector 120. Because the translating devices 115 and 125 embodied as robot arms have their sensors preferably built in, it is possible to rely solely on these intrinsic sensors, plus some system calibration information identifying where the translating devices 115 and 125 are in the motion capture device 140 space, to get all the required position information for system operation. As a result, the motion capture device 140 can obtain position information regarding source 110 and detector 120 directly from the robot sensors.

When the robotic translating devices 115 and 125 are stationary, having motion capture devices on the stationary robotic translating devices 115 and 125 generally provides redundant information. However, this arrangement provides robustness and flexibility for system 100. If the robotic translating devices 115 and 125 are mobile, then having motion capture devices on translating devices 115 and 125 would be generally required.

In one embodiment, position markers 145 provide light, such as by reflection or photoluminescence, in response to emissions received from an optical emitter included within motion capture device 140 which includes an optical tracking system (not shown). Thus, in this embodiment, motion capture device 140 provides both an optical emitter and a detector.

In an alternate related embodiment, optical markers 145 can be self-illuminating. In this embodiment, the motion capture device 140 can comprise only detectors. Data from motion capture device 140 is transmitted to computing device (not shown) which includes memory, which is preferably a non-volatile memory, such as a disk-drive.

The markers can be light emitting diodes (LEDs), or retro reflective spherical passive markers. Optical markers 145 are not required for motion capture device 140 positional tracking. For example, as an alternative to optical markers 145, electromagnetic, acoustic, and other video based tracking technologies can be used with the invention.

Conventional imaging systems use an x-ray source and image detector mounted in a fixed relationship, typically utilizing a fixed center of rotation with respect to the scan area. FIG. 2(b) shows the scan volume provided by a conventional computed tomography systems which uses a center of rotation midway between the source and sensor, providing for simple physical structures and reconstruction geometries. In contrast, FIG. 2(a) shows the scan volume provided by a system according to the invention which allows unrestricted motion of the source relative to the detector which as a result can provide greater scan volumes (shaded) for the same source-sensor distance, and also provide a platform for exploring novel scan paths and reconstruction strategies. Mounting the x-ray source and image detector on separate translating structures according to the invention thus provides a new opportunity to explore generalized scan paths with the potential to increase scan volume and reduce object shape related artifacts.

FIG. 3 shows a schematic diagramming the communication architecture of an exemplary dynamic imaging system 300 according to the invention. Each robot 115 and 125 has associated robot controllers 116 and 126, respectively, can use intrinsic sensors and extrinsic feedback for control inputs. Control in the form of beam gating 370 of x-ray source 110 and movement of robots 115 and 125 derives from the real-time motion capture data provided by motion capture module 145 to trajectory planning modules 155. Optical alignment feedback 310 can be used in non-human accuracy assessment and trajectory development functions, but is not preferably used in clinical studies to minimize radiation exposure. Motion capture and robot intrinsic sensors are preferably used in clinical studies.

Performance requirements for the motion capture device and robotic-based translation systems are based on the dynamics of the activities being tracked. The motion capture device preferably provides real-time 3D position measurements of approximately 20 spatial locations at a minimum of 100 Hz and preferably at least 500 Hz. Higher frame rates will permit higher bandwidth robot control and better dynamic response. There are several commercially available motion capture systems meeting this specification, including systems from Northern Digital Inc., Motion Analysis Corp., and PhaseSpace, Inc.

Gait and stair-climbing are activities which have the high movement velocities and cover the largest volumes of space. Motion laboratory data for healthy normal subjects can be used to define the upper bounds for imaging volume and accelerations at the robot endpoints. From this data, peak accelerations of approximately 1 g will be required to track the knee joint through space for the entire gait cycle. Gait covers approximately 1 m per step as does stair-climbing, so the working volume of each robot will need to be at least 1 m on a side. Based on these performance requirements and the system definitions, a robot with a 10 kg payload (e.g. Mitsubishi PA10, FIG. 4) will meet the needs for actuation of a 5 kg image sensor. Actuation of an x-ray source, which can weigh 6-50 kg, will require a different approach.

X-ray sources typically weigh 6 kg to 50 kg and require high voltage power cables which are stiff and heavy. A robot capable of handing this payload as a dead weight would be an industrial unit, and likely lacking easy portability or open programmability for real-time high performance. In one embodiment, the high-voltage cables 410 are suspended and a counter-weight mechanism 430 from a low friction gantry mounted over the workspace of a small robot 455 as shown in FIG. 4 is used to carry the vertical loads of the imaging system hardware. In another embodiment, the suspension system is comprised of an automatic controller, motor and winch, carrying the dynamic vertical component of the x-ray source payload 455. This gravity compensation will reduce the mechanical demands on the robot approximately to inertial loads plus friction. Ceiling suspended equipment is common and generally preferred in hospital and clinical settings to maximize floor-plan flexibility and sanitary maintenance.

More than 35 million Americans, as well as hundreds of millions worldwide, suffers from disabling musculoskeletal conditions. Systems according to the invention will provide a new tool for quantifying joint injury or disease and assessing the efficacy of surgical treatments. The types of activities and anatomic locations the system is capable of imaging dynamically are varied. These applications include the knee, tibio-femoral motions during normal gait, rising and sitting in a chair, climbing and descending stairs and patello-femoral motions in the transverse plane during chair rise/sit, kneeling and squatting or pedaling. Applied to the hip, femoro-acetabular motions during normal gait, rising from a chair, moving into a cross-legged position, and squatting can also be obtained. The invention can be applied to the spine, lumbar spine during lifting and turning motions, such as during a golf swing motion. Regarding the shoulder, gleno-humeral motion during overhead motions including hair combing, lifting and slow throwing can be obtained. Regarding the foot/ankle, tibio-talar and mid-foot motions during gait can also be obtained.

The invention thus provides new capabilities to examine the skeleton in motion, during weight-bearing dynamic activity, providing new capabilities for measurement and diagnosis. In addition, the invention provides the ability to perform CT scans in a smaller, lighter, potentially less expensive format than is currently available. Having both capabilities in a single system is unique, and potentially makes it possible for more facilities to afford highly capable medical diagnostic equipment.

This invention can be embodied in other forms without departing from the spirit or essential attributes thereof and, accordingly, reference should be had to the following claims rather than the foregoing specification as indicating the scope of the invention.

The invention claimed is:

1. A radiographic imaging system, comprising:
a penetrating radiation source including a first translating device, said first translating device comprising a first controller for positioning said radiation source;
a radiation image detector including a second translating device positioned on a side of a subject to be imaged opposite said radiation source, said second translating device comprising a second controller for positioning said detector, wherein radiation from said radiation source passes through said region of said subject to said detector; and
a motion capture device communicably connected to both said first and second controllers, said motion capture device tracking a position of said region of said subject and providing position information to both said first controller and second controllers for dynamically coordinating positions of said radiation source and said radiation detector for obtaining an image of said region
wherein said system provides unrestricted motion of said source relative to said detector;
wherein said system provides cone-beam computed tomography using imaging paths including paths other than a center of rotation located midway between said the source and said detector.

2. The system of claim 1, wherein said motion capture device is spaced apart from said subject.

3. The system of claim 1, wherein said first and second translating devices comprise robotic arms, said robotic arms including structure for moving said robotic arms, said robotic arms including at least one position sensor.

4. The system of claim 1, wherein said motion capture device obtains real time position data for said region of said subject, said system utilizing said real time-data to dynamically guide said first and second controllers.

5. The system of claim 1, wherein said system further comprises at least one of a first force/torque sensor disposed between an endpoint of said first translating device and said radiation source and a second force/torque sensor disposed between an endpoint of said second translating device said radiation detector.

6. The system of claim 1, further comprising an overhead suspension system to carry a vertical load of at least one of said penetrating radiation source including said first translating device and said radiation detector including said second translating device.

7. A method of obtaining images, comprising the steps of:
providing a radiographic imaging system which includes a movable and independently positionable penetrating radiation source and radiation image detector;
obtaining dynamic radiographic images of the skeleton of a subject while said subject is in motion using said system, wherein movement of said source and detector is based on motion of said subject to obtain a plurality of aligned views to obtain an image of said subject; and obtaining tomographic scans of said subject, said tomographic scans providing 3D anatomic reconstruction of said subject.

8. The method of claim 7, wherein said image detector is placed in contact and remains in contact with said subject during said obtaining of said dynamic radiographic images.

9. The method of claim 8, wherein said images are recorded during weight-bearing activity by said subject.

10. The method of claim 7, further comprising the steps of obtaining real-time position data for said subject, and utilizing said real time-data to dynamically guide positions of said penetrating radiation source and said radiation image detector.

* * * * *